(12) United States Patent
Alam

(10) Patent No.: US 10,518,070 B1
(45) Date of Patent: Dec. 31, 2019

(54) DEVICE FOR POWDERING A SOLID UNIT DOSAGE FORM OF MEDICATION AND ADMINISTERING THE POWDER FORM

(71) Applicant: KING SAUD UNIVERSITY, Riyadh (SA)

(72) Inventor: Mohd Aftab Alam, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/361,093

(22) Filed: Mar. 21, 2019

(51) Int. Cl.
*A61M 31/00* (2006.01)

(52) U.S. Cl.
CPC ....... *A61M 31/00* (2013.01); *A61M 2202/066* (2013.01); *A61M 2210/1064* (2013.01); *A61M 2210/1475* (2013.01)

(58) Field of Classification Search
CPC .......... A61M 2202/066; A61M 31/007; A61M 37/0069; A61M 2210/1064; A61M 2210/1475; A61J 7/0007; A61J 3/02
See application file for complete search history.

(56) References Cited

U.S. PATENT DOCUMENTS

| | | | |
|---|---|---|---|
| 2,622,594 A | 12/1952 | Brooks | |
| 2,722,935 A | 11/1955 | Thompson et al. | |
| 2,946,332 A | 7/1960 | Sacks | |
| 3,424,158 A * | 1/1969 | Silver | A61D 7/00 604/514 |
| 4,209,136 A * | 6/1980 | Linden | A61J 7/0007 241/169.2 |
| 5,123,915 A * | 6/1992 | Miller | A61J 7/0007 604/77 |
| 5,322,227 A * | 6/1994 | Fiocchi | A61J 7/0007 241/100 |
| 5,376,072 A * | 12/1994 | Klearman | A61J 7/0007 604/218 |
| 5,673,685 A | 10/1997 | Heide et al. | |
| 7,591,808 B2 | 9/2009 | DiPiano et al. | |
| 9,204,704 B1 | 12/2015 | Wolfe | |
| 9,795,773 B2 | 10/2017 | Boyes et al. | |
| 2006/0004318 A1* | 1/2006 | Przepasniak | A61M 31/00 604/14 |
| 2006/0151644 A1* | 7/2006 | Smith | A61J 7/0007 241/30 |

(Continued)

FOREIGN PATENT DOCUMENTS

GB 2311726 A 10/1997

*Primary Examiner* — Rebecca E Eisenberg
*Assistant Examiner* — Tasnim Mehjabin Ahmed
(74) *Attorney, Agent, or Firm* — Richard C. Litman; Nath, Goldberg & Meyer

(57) ABSTRACT

The device for powdering a solid unit dosage form of medication and administering the powder form includes an applicator, a powdering tool and, in certain embodiments, a cap. The device is used to create a powder form from a solid unit dosage form, and then administer the powder form to a body cavity of a patient. The cap is provided with an integrated powdering tool, allowing an open end of an applicator barrel to be releasably covered thereby. Manipulation of the powdering tool creates the powder form through abrasion of a solid unit dosage form of the medication received within the barrel. The cap and powdering tool may then be removed, leaving the powder form of the solid unit dosage form to be administered to the body cavity, such as a patient's vagina or rectum.

17 Claims, 4 Drawing Sheets

(56) References Cited

U.S. PATENT DOCUMENTS

| | | |
|---|---|---|
| 2010/0010471 A1 | 1/2010 | Ladd et al. |
| 2011/0066137 A1 | 3/2011 | Parks et al. |
| 2015/0164735 A1* | 6/2015 | Gallant ................. A61F 13/266 600/38 |

* cited by examiner

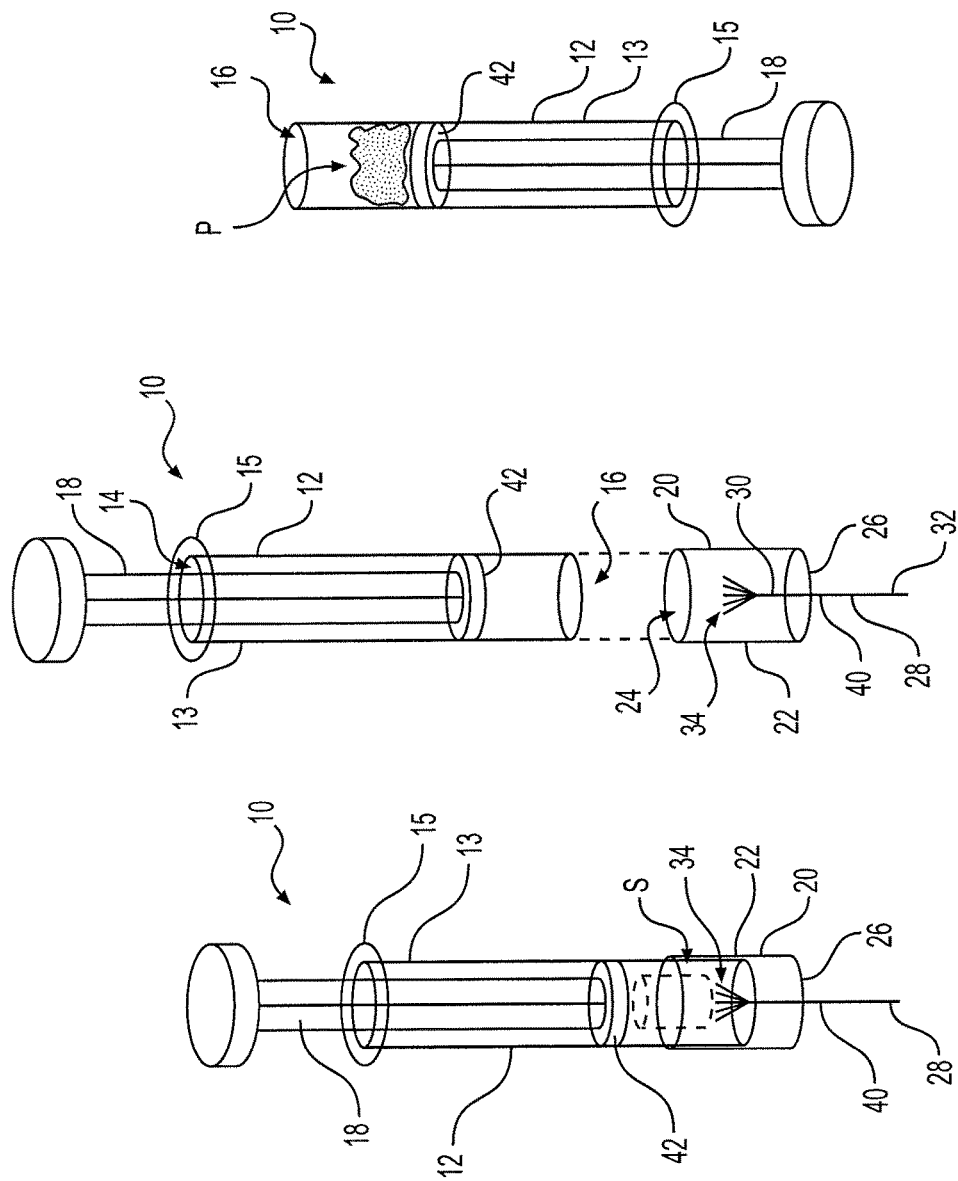

DEVICE FOR POWDERING A SOLID UNIT DOSAGE FORM OF MEDICATION AND ADMINISTERING THE POWDER FORM

BACKGROUND

1. Field

The disclosure of the present patent application relates to the administration of pharmaceutical preparations, and particularly to a device for powdering a solid unit dosage form of medication and administering the powder form of the solid unit dosage form into a body cavity of a patient.

2. Description of the Related Art

A wide variety of applicators have been used for administering pharmaceutical preparations to body cavities, such as to a patient's rectum or vagina. Such pharmaceutical preparations are typically provided in cream or gel form, or in the form of a solid unit dosage, such as a tablet, caplet, capsule or the like. For administering semi-solid dosage forms (such as gels or creams) or solid unit dosage forms (such as tablets or capsules), the pharmaceutical preparation is typically placed in the barrel of an applicator, which is shaped for insertion in the rectum or vagina. An actuator, such as a plunger, is then manually operated to administer the pharmaceutical preparation into the body cavity. The semi-solid dosage forms, such as gels and creams, easily spread in the body cavity under pressure generated by the collapsible walls of body cavity. However, there are some drawbacks of solid unit dosage forms (especially tablets) which are meant to be administered into the body cavity. The disintegration of solid unit dosage forms is slow in the vaginal or rectal cavity because of the limited amount of liquid media in the vaginal or rectal cavity. Additionally, sometimes, the solid unit dosage form slipped out before complete disintegration in the body cavity.

In order to prevent such inherent problems of slow disintegration and slipping out of the solid unit dosage form, a device is desired which can solve the problem of slow disintegration and premature slipping out of the solid unit dosage form from the body cavity. The device will convert the solid unit dosage form into powder form and then the powder form will be administered into body cavity using applicator of same device. The powder form of the solid unit dosage form will be distributed over a larger surface area within the cavity. Thus, a device for powdering a solid unit dosage form of medication and administering the powder form solving the aforementioned problems is desired.

SUMMARY

The device for powdering a solid unit dosage form of medication and administering the powder form creates a powder form from a solid unit dosage form, and further provides an applicator tool for administering the powder form into a body cavity of a patient. As used herein, the "solid unit dosage form" refers to conventional dosage forms, such as commonly provided in the form of tablets, caplets, capsules or the like. Further, as used herein, the "powder form" refers to the converted powder and/or particulate matter created from powdering, grinding, abrading or crushing the solid unit dosage form. The device for powdering a solid unit dosage form of medication and administering the powder form may be used to first create a powder form from a single dose of solid medication, and then administer the powder form to the rectum or vagina of a patient, for example, in a manner similar to a conventional vaginal or rectal applicator for gels, creams or powders, typically including a plunger and a barrel.

The device for powdering a solid unit dosage form of medication and administering the powder form includes an applicator and a powdering tool. The applicator includes a barrel, having a sidewall, a flange, first and second open ends, and a plunger slidably received within the barrel and at least partially projecting through the first open end thereof. The barrel and plunger are similar to those of a conventional syringe or medication applicator used for administering a pharmaceutical preparation into a patient's rectum or vagina. A cap is provided for holding and operating a powdering tool to create the powder form from the solid unit dosage form. The cap has at least one sidewall, an open end and a closed end. The powdering tool includes a shaft having opposed first and second ends. The shaft extends through the closed end of the cap such that the first end of the shaft is positioned within the cap and the second end of the shaft is positioned exterior to the cap. The dimensions (diameter and length) of the second end of the shaft are suitable to hold and operate the powdering tool with ease. At least one abrading element is secured to, and projects from, the first end of the shaft.

In use, the cap is releasably secured to the barrel to removably cover the second open end thereof. The at least one abrading element of the powdering tool is then used to create the powder form from a solid unit dosage form received within the barrel between the closed end of the cap and a slidable seal of the plunger. The closed end of the cap may be resilient or flexible, allowing the user to grip the second end of the shaft and move the shaft to scrape the at least one abrading element against the solid unit dosage form. Once the solid unit dosage form has been fully powdered, the barrel may be turned over such that the open second end thereof faces upward (to keep the powder form within the barrel, between the open second end and the slidable seal of the plunger), and the cap may be removed. The open second end of the barrel may then be inserted into the body cavity of the patient for administering the powder form, using the slidable plunger in a manner similar to a conventional plunger-driven or syringe-type applicator.

In an alternative embodiment, the cap is replaced by a plug having opposed first and second ends. The powdering tool is similar to that described above, including a shaft having opposed first and second ends, where the shaft extends through the plug such that the second end of the shaft is positioned exterior to the plug. At least one abrading element is secured to, and projects from, the first end of the shaft. The plug is releasably secured to the barrel to removably seal the second open end thereof. The at least one abrading element of the powdering tool is removably received within the barrel to create the powder form from the solid unit dosage form received within the barrel between the first end of the plug and the slidable seal of the plunger. The plug may be formed from a resilient material, and at least one horizontal slot may be formed therethrough for selective pivoting of the shaft of the powdering tool.

These and other features of the present invention will become readily apparent upon further review of the following specification.

BRIEF DESCRIPTION OF THE DRAWINGS

FIG. 1 is a perspective view of a device for powdering a solid unit dosage form of medication and administering the powder form.

FIG. 2 is a partially exploded view of the device of FIG. 1, showing the powdering tool detached from the barrel.

FIG. 3 is a perspective view of the device of FIG. 1, shown configured for administering the powder form to a patient's body cavity.

Similar reference characters denote corresponding features consistently throughout the attached drawings.

DETAILED DESCRIPTION OF THE PREFERRED EMBODIMENTS

Figure 7:
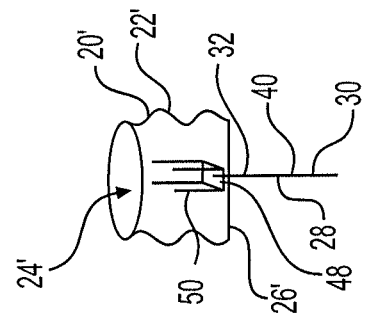
FIG. 7 is a perspective view of still another alternative embodiment of a cap and powdering tool combination of a device for powdering a solid unit dosage form of medication and administering the powder form.

The device for powdering a solid unit dosage form of medication and administering the powder form, designated generally as 10 in the drawings, creates a powder form from a solid unit dosage form and provides an applicator tool for administering the powder form into a body cavity of a patient. For example, the device for powdering a solid unit dosage form of medication and administering the powder form 10 may be used to first create a powder form P of the solid unit dosage form S, and then administer the powder form P to the rectum or vagina of a patient in a manner similar to conventional administration of dosage forms (e.g., gels, creams and powders) using a vaginal or rectal applicator having a plunger and a barrel. As used herein, the "solid unit dosage form" refers to conventional dosage forms, such as commonly provided in the form of tablets, caplets, capsules or the like. Further, as used herein, the "powder form" refers to the converted powder and/or particulate matter created from powdering, grinding, abrading or crushing the solid unit dosage form.

As shown in FIGS. 1-3, the device for powdering a solid unit dosage form of medication and administering the powder form 10 includes a barrel 12, having a sidewall 13 and first and second open ends 14, 16, respectively. As with a conventional syringe-type applicator, barrel 12 may be provided with a flange 15. As will be described in greater detail below, a plunger, cap and powdering tool are also provided. The plunger 18 is slidably disposed within the barrel 12 and at least partially projects through the first open end 14. The barrel 12 and plunger 18 are similar to those of a conventional syringe or medication applicator. A cap 20 is provided for holding and operating a powdering tool 40 to create the powder form P from the solid unit dosage form S. The cap 20 has at least one sidewall 22, an open end 24 and a closed end 26. The powdering tool 40 includes a shaft 28 having opposed first and second ends 30, 32, respectively. The shaft 28 extends through the closed end 26 of the cap 20 such that the first end 30 of the shaft 28 is positioned within the cap 20 and the second end 32 of the shaft 28 is positioned exterior to the cap 20. At least one abrading element 34 is secured to and projects from the first end 30 of the shaft 28. In the embodiment of FIGS. 1-3, the at least one abrading element 34 is shown as a plurality of prongs. It should be understood that any suitable type of abrading element may be used, and it should be further understood that the overall configuration, number and relative dimensions of the prongs shown in FIGS. 1-3 are shown for exemplary and illustrative purposes only.

As shown in FIG. 1, in use, the cap 20 is releasably secured to the barrel 12 to removably cover the second open end 16. The at least one abrading element 34 of the powdering tool 40 is then used to create the powder form P (as shown in FIG. 3) from a solid unit dosage form S received within the barrel 12, between the closed end 26 of the cap 20 and a slidable seal 42 of the plunger 18. It should be understood that the tablet shown in FIG. 1 is shown for exemplary purposes only, and that the powdering tool 40 may be used to create powder from any suitable type of solid unit dosage form, such as a hard capsule, caplet, or the like.

The closed end 26 of the cap 20 may be resilient or flexible, allowing the user to effectively move the shaft 28 to scrape the at least one abrading element 34 against the solid unit dosage form S. Once the solid unit dosage form S has been fully powdered, the barrel 12 may be turned over such that the open second end 16 thereof faces upward, as shown in FIG. 3, in order to keep the powder form P within the barrel 12 between the open second end 16 and the slidable seal 42 of the plunger 18. The cap 20 is removed from barrel 12 such that the open second end 16 of the barrel 12 may then be inserted into the body cavity of the patient for administering the powder form P of the solid unit dosage form S, using the slidable plunger 18 in a manner similar to a conventional plunger-driven or syringe-type applicator.

Figure 5:
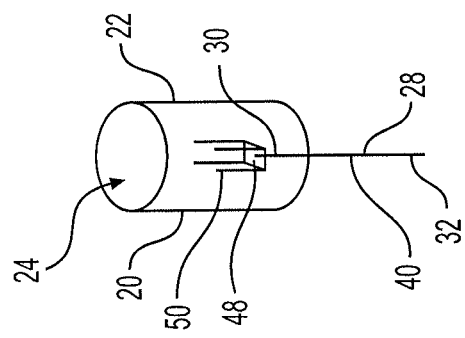
FIG. 5 is a perspective view of another alternative embodiment of a cap and powdering tool combination of a device for powdering a solid unit dosage form of medication and administering the powder form.
Figure 4:
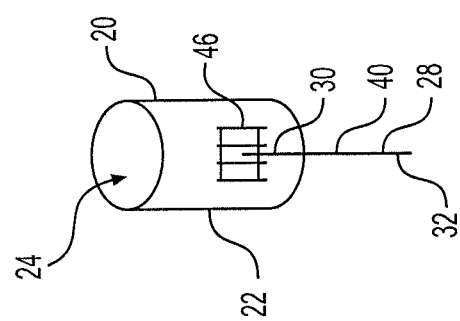
FIG. 4 is a perspective view of an alternative embodiment of a cap and powdering tool combination of a device for powdering a solid unit dosage form of medication and administering the powder form.
Figure 8:
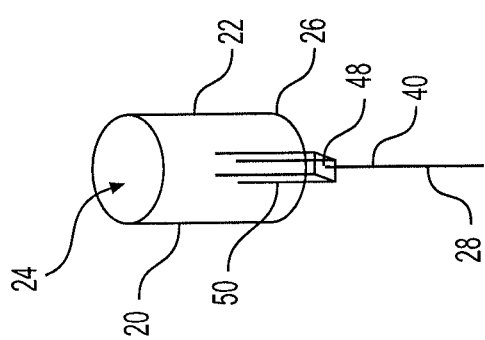
FIG. 8 is a perspective view of yet another alternative embodiment of a cap and powdering tool combination of a device for powdering a solid unit dosage form of medication and administering the powder form.

As noted above, it should be understood that any suitable type of abrading element may be used. FIG. 4 shows a powdering tool 40 (in combination with cap 20) with the prongs 34 of FIGS. 1 and 2 replaced by blades 46. In another embodiment, shown in FIG. 5, a plate 48 is mounted on the first end 30 of the shaft 28 with the at least one abrading element 50 projecting outward from the plate 48. In FIG. 5, the abrading element 50 is again shown as a plurality of prongs. However, it should be understood that the overall configuration, number and relative dimensions of the prongs shown in FIG. 5 are shown for exemplary and illustrative purposes only. The alternative embodiment of FIG. 8 is similar to that of FIG. 5, but in the embodiment of FIG. 8, the plate 48 is positioned external to the cap 20, with the prongs 50 extending through the resilient closed end 26 of the cap 20.

Figure 6:
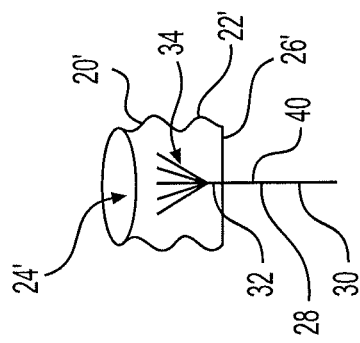
FIG. 6 is a perspective view of a further alternative embodiment of a cap and powdering tool combination of a device for powdering a solid unit dosage form of medication and administering the powder form.

In the further alternative embodiment of FIG. 6, the cap 20 of the previous embodiments has been replaced by cap 20', which includes an open end 24', a closed end 26' and a sidewall 22'. In the embodiment of FIG. 6, the powdering tool 40 of FIGS. 1 and 2 is shown in combination with the cap 20'. Cap 20' is similar to cap 20, but the sidewall 22' and closed end 26' are both formed of a resilient or flexible material. Thus, in use, the user may grasp and manipulate both the shaft 28 and the cap 20' in order to powder the solid unit dosage form S. It should be understood that the cap 20' may be used in combination with any of the abrading elements described above. In a further embodiment, FIG. 7 shows the cap 20' being used in combination with the powdering tool 40 of FIG. 5.

Figure 9:
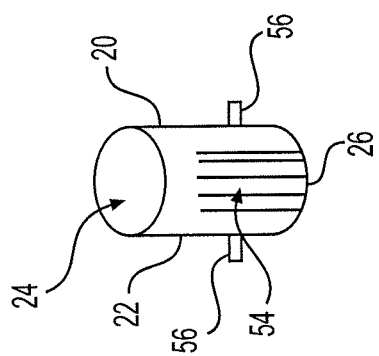
FIG. 9 is a perspective view of an alternative embodiment of a cap of a device for powdering a solid unit dosage form of medication and administering the powder form.

FIG. 9 shows a further alternative embodiment in which the powdering tool 40 has been removed from the cap 20. In the embodiment of FIG. 9, at least one abrading element 54 (shown here as a plurality of prongs) is attached directly to the rigid closed end 26 of the cap 20, within the interior of the cap 20. As shown, a pair of gripping members 56 may be secured to the sidewall 22 of the cap 20, allowing the user to twist and manipulate the cap 20 for powdering the solid unit dosage form S. It should be understood that any suitable type of abrading element may be used, and it should be further understood that the overall configuration, number and relative dimensions of the prongs 54 shown in FIG. 9 are shown for exemplary and illustrative purposes only.

Figure 10:
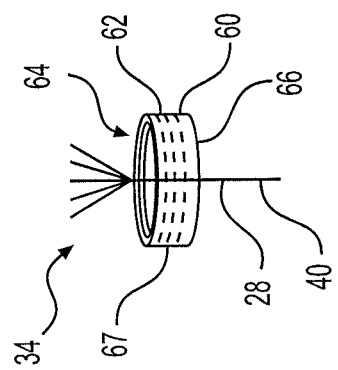
FIG. 10 is a perspective view of another alternative embodiment of a cap and powdering tool combination of a device for powdering a solid unit dosage form of medication and administering the powder form.

In the alternative embodiment of FIG. 10, the powdering tool 40 is used in combination with an alternative cap 60. As shown, the cap 60 may have a lower profile than the cap 20, resulting in the at least one abrading element 34 being positioned above the open end 64 and sidewall 62 of the cap 60. The cap 60 may have a resilient closed end 66, allowing the cap 60 to be used in combination with the powdering tool 40 in a manner similar to that described above with respect to the previous embodiments. As shown, internal threads 67 may be formed on an inner face of the sidewall 62, allowing the cap 60 to securely and releasably engage corresponding external threads formed on the barrel 12 adjacent the second end 16 thereof. FIG. 10 shows the powdering tool 40 of FIGS. 1 and 2 being used in combination with the cap 60. It should be understood that any suitable type of abrading element may be used, including those described above with regard to the previous embodiments. It should be further understood that the overall configuration, number and relative dimensions of the prongs 34 shown in FIG. 10 are shown for exemplary and illustrative purposes only.

Figure 11:
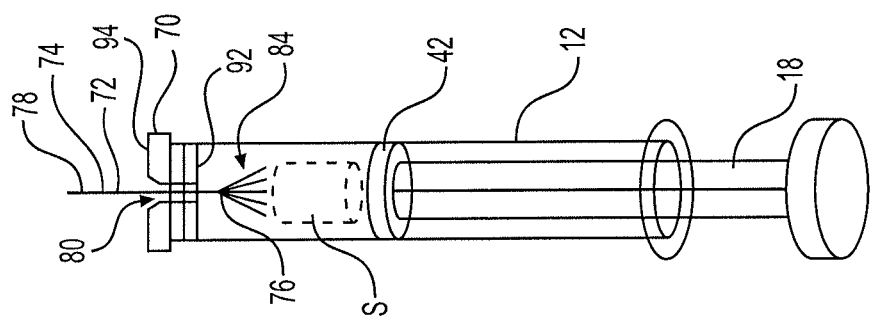
FIG. 11 is a perspective view of an alternative embodiment of a device for powdering a solid unit dosage form of medication and administering the powder form.

In the further alternative embodiment of FIG. 11, the cap 20 is replaced by a plug 70 having opposed first and second ends 92, 94, respectively. The powdering tool 72 is similar to that described above, including a shaft 74 having opposed first and second ends 76, 78, respectively, where the shaft 74 extends through the plug 70 such that the second end 78 is positioned exterior to plug 70. At least one abrading element 84 is secured to and projects from the first end 76 of the shaft 74. In FIG. 11, the powdering tool 72 is shown as being similar to the powdering tool 40 of FIGS. 1 and 2. However, it should be understood that any of the powdering tools described in the previous embodiments may be used in combination with the plug 70. It should be further understood that the overall configuration and relative dimensions of the plug 70 are shown in FIG. 11 for exemplary purposes only.

The plug 70 is releasably secured to the barrel 12 to removably seal the second open end 16 thereof. The at least one abrading element 84 of the powdering tool 72 is removably received within the barrel 12 to create the powder form P from solid unit dosage form S within the barrel 12, between the first end 92 of the plug 70 and the slidable seal 42 of the plunger 18, as in the previous embodiments. The plug 70 may be formed from a resilient material, and at least one horizontal slot 80 may be formed therethrough for selective pivoting of the shaft 74 of the powdering tool 72.

Figure 12:
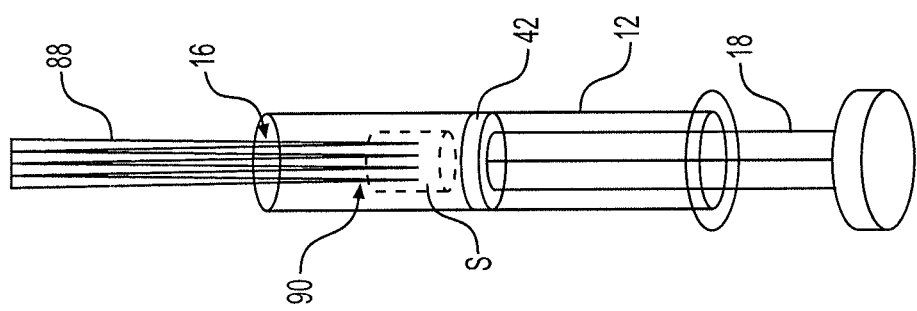
FIG. 12 is a perspective view of another alternative embodiment of a device for powdering a solid unit dosage form of medication and administering the powder form.

FIG. 12 illustrates an additional alternative embodiment that eliminates the need for a cap or plug, as in the previous embodiments. In FIG. 12, an abrading tool 88 is provided for direct holding and manipulation by the user. Tip 90 of the abrading tool 88 is inserted directly into the open second end 16 of the barrel 12 for powdering the solid unit dosage form S. The embodiment of FIG. 12 shows the abrading tool 88 as four sharp prongs secured to one another. However, it should be understood that any suitable type of abrading element may be used, including those described above with regard to the previous embodiments. It should be further understood that the overall configuration, number and relative dimensions of the sharp prongs shown in FIG. 12 are shown for exemplary and illustrative purposes only.

It is to be understood that the device for powdering a solid unit dosage form of medication and administering the powder form is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A device for powdering a solid unit dosage form of medication and administering the powder form, consisting of:
   a barrel having a sidewall and first and second open ends;
   a plunger slidably disposed within the barrel and at least partially projecting through the first open end thereof;
   a cap having an imperforate sidewall, an open end and a closed end, the cap being releasably attachable to the barrel to removably cover the second open end of the barrel; and
   a powdering tool having:
      a shaft having opposed first and second ends, the shaft extending through the closed end of the cap so that the first end of the shaft is positioned within the cap and the second end of the shaft is positioned exterior to the cap; and
      at least one abrading element extending from the first end of the shaft into the barrel when the cap is attached to the second end of the barrel, the powdering tool being adapted for powdering a solid unit dosage form of medication placed between the cap and the plunger by manipulation of the shaft to create a powder form of the solid unit dosage form for administration into a body cavity of a patient by inserting the second end of the barrel into the body cavity after removal of the cap from the barrel and sliding the plunger in the barrel, wherein the at least one abrading element is the sole abrading element configured for powdering the solid unit dosage form of medication.

2. The device for powdering a solid unit dosage form of medication and administering the powder form as recited in claim 1, wherein the closed end of the cap is resilient.

3. The device for powdering a solid unit dosage form of medication and administering the powder form as recited in claim 1, wherein the at least one abrading element comprises at least one prong.

4. The device for powdering a solid unit dosage form of medication and administering the powder form as recited in claim 1, wherein the at least one abrading element comprises at least one blade.

5. The device for powdering a solid unit dosage form of medication and administering the powder form as recited in claim 1, wherein the powdering tool further comprises a plate mounted on the first end of the shaft, the at least one abrading element extending from the plate.

6. The device for powdering a solid unit dosage form of medication and administering the powder form as recited in claim 1, wherein the closed end and the sidewall of the cap are each resilient.

7. A device for powdering a solid unit dosage form of medication and administering the powder form, consisting of:
   a barrel having a sidewall and first and second open ends;
   a plunger slidable within the barrel and at least partially projecting through the first open end of the barrel;
   a cap having an imperforate sidewall, an open end, and a closed end, the cap being releasably secured to the barrel to removably cover the second open end of the barrel; and
   a powdering tool having:
      a shaft having opposed first and second ends, the shaft extending through the closed end of the cap so that the second end of the shaft is positioned exterior to the cap; and
      at least one abrading element extending from the first end of the shaft, the at least one abrading element being adapted for removable insertion within the barrel to powder a solid unit dosage form of medication placed between the closed end of the cap and the plunger to create a powder form of the solid unit dosage form, the device being adapted for administering the powder form into a body cavity of a patient by inserting the second end of the barrel into the body cavity and sliding the plunger in the barrel, wherein the at least one abrading element is the sole abrading element configured for powdering the solid unit dosage form of medication.

8. The device for powdering a solid unit dosage form of medication and administering the powder form as recited in claim 7, wherein the closed end of the cap is resilient.

9. The device for powdering a solid unit dosage form of medication and administering the powder form as recited in claim 7, wherein the at least one abrading element comprises at least one prong.

10. The device for powdering a solid unit dosage form of medication and administering the powder form as recited in claim 7, wherein the at least one abrading element comprises at least one blade.

11. The device for powdering a solid unit dosage form of medication and administering the powder form as recited in claim 7, wherein the powdering tool further comprises a plate mounted on the first end of the shaft, the at least one abrading element projecting outward from the plate.

12. A device for powdering a solid unit dosage form of medication and administering the powder form, consisting of:
   a barrel having a sidewall and first and second open ends;
   a plunger slidably received within the barrel and at least partially projecting through the first open end of the barrel;
   a plug having an imperforate sidewall and opposed first and second ends, the plug being releasably attached to the barrel to removably seal the second open end of the barrel; and
   a powdering tool having:
      a shaft having opposed first and second ends, the shaft extending through the plug so that the second end of the shaft is positioned exterior to the plug; and
      at least one abrading element secured to and projecting from the first end of the shaft so that the at least one abrading element is adapted to powder a solid unit dosage form of medication inside the barrel by manipulation of the second end of the shaft when the plug is attached to the barrel to create a powder form of the solid unit dosage form, the device being adapted for administering the powder form into a body cavity of a patient by inserting the second end of the barrel into the body cavity and sliding the plunger in the barrel, wherein the at least one abrading element is the sole abrading element configured for powdering the solid unit dosage form of medication.

13. The device for powdering a solid unit dosage form of medication and administering the powder form as recited in claim 12, wherein the plug is resilient.

14. The device for powdering a solid unit dosage form of medication and administering the powder form as recited in claim 13, wherein the plug has at least one horizontal slot formed therethrough for selective pivoting of the shaft of the powdering tool.

15. The device for powdering a solid unit dosage form of medication and administering the powder form as recited in claim 12, wherein the at least one abrading element comprises at least one prong.

16. The device for powdering a solid unit dosage form of medication and administering the powder form as recited in claim 12, wherein the at least one abrading element comprises at least one blade.

17. The device for powdering a solid unit dosage form of medication and administering the powder form as recited in claim 12, wherein the powdering tool further comprises a plate mounted on the first end of the shaft, the at least one abrading element projecting outward from the plate.

* * * * *